US010898087B2

(12) United States Patent
Gunturi et al.

(10) Patent No.: US 10,898,087 B2
(45) Date of Patent: Jan. 26, 2021

(54) MOTION DETECTION AND CANCELLATION USING AMBIENT LIGHT

(71) Applicant: TEXAS INSTRUMENTS INCORPORATED, Dallas, TX (US)

(72) Inventors: Sarma Sundareswara Gunturi, Bangalore (IN); Jaiganesh Balakrishnan, Bangalore (IN)

(73) Assignee: TEXAS INSTRUMENTS INCORPORATED, Dallas, TX (US)

(*) Notice: Subject to any disclaimer, the term of this patent is extended or adjusted under 35 U.S.C. 154(b) by 543 days.

(21) Appl. No.: 15/835,646

(22) Filed: Dec. 8, 2017

(65) Prior Publication Data
US 2019/0175037 A1 Jun. 13, 2019

(51) Int. Cl.
A61B 5/024 (2006.01)
A61B 5/00 (2006.01)

(52) U.S. Cl.
CPC ...... A61B 5/02438 (2013.01); A61B 5/02444 (2013.01); A61B 5/681 (2013.01); A61B 5/721 (2013.01); A61B 2503/10 (2013.01)

(58) Field of Classification Search
CPC . A61B 5/02438; A61B 5/02444; A61B 5/681; A61B 5/721; A61B 2503/10
USPC ...................................................... 600/502
See application file for complete search history.

(56) References Cited

U.S. PATENT DOCUMENTS

| 8,888,701 | B2* | 11/2014 | LeBoeuf | G16Z 99/00 |
| | | | | 600/301 |
| 9,814,400 | B1* | 11/2017 | Cendrillon | A61B 5/02438 |
| 9,826,940 | B1* | 11/2017 | Lengerich | A61B 5/721 |
| 10,251,571 | B1* | 4/2019 | Cendrillon | A61B 5/02438 |
| 10,602,981 | B2* | 3/2020 | Karnik | A61B 5/7267 |
| 2006/0094943 | A1 | 5/2006 | Van Slyke | |
| 2006/0122476 | A1 | 6/2006 | Van Slyke | |
| 2007/0213619 | A1 | 9/2007 | Linder | |
| 2008/0287815 | A1 | 11/2008 | Chon et al. | |
| 2010/0081946 | A1 | 4/2010 | Garudadri et al. | |
| 2010/0228136 | A1 | 9/2010 | Keel et al. | |
| 2010/0324384 | A1 | 12/2010 | Moon et al. | |
| 2010/0324385 | A1 | 12/2010 | Moon et al. | |
| 2010/0324386 | A1 | 12/2010 | Moon et al. | |
| 2010/0324387 | A1 | 12/2010 | Moon et al. | |
| 2010/0324388 | A1 | 12/2010 | Moon et al. | |
| 2010/0324389 | A1 | 12/2010 | Moon et al. | |
| 2011/0066041 | A1 | 3/2011 | Pandia et al. | |

(Continued)

Primary Examiner — Navin Natnithithadha
(74) Attorney, Agent, or Firm — John R. Pessetto; Charles A. Brill; Frank D. Cimino

(57) ABSTRACT

An apparatus to detect a heart rate of a user includes a motion detection circuit configured to generate a motion status signal indicative of a motion status of the user. The apparatus also comprises a filter circuit coupled to the motion detection circuit that is configured to generate a filter circuit output signal based on dynamically variable. The coefficients are dependent on the motion status signal and a first signal received by the filter circuit. The apparatus also comprises a combination circuit coupled to the filter circuit and configured to receive a second signal indicative of the ambient light, the motion of the user, and non-ambient light reflected from the user. The combination circuit is configured to determine a difference between the second signal and the filter circuit output signal to generate a combination circuit output signal.

11 Claims, 3 Drawing Sheets

(56) References Cited

U.S. PATENT DOCUMENTS

| | | |
|---|---|---|
| 2011/0066042 A1 | 3/2011 | Pandia et al. |
| 2011/0098583 A1 | 4/2011 | Pandia et al. |
| 2012/0197093 A1* | 8/2012 | LeBoeuf ............ G16H 40/63 600/301 |
| 2013/0171599 A1 | 7/2013 | Bleich et al. |
| 2013/0172760 A1 | 7/2013 | Chon et al. |
| 2013/0276785 A1 | 10/2013 | Melker et al. |
| 2014/0088385 A1 | 3/2014 | Moon et al. |
| 2014/0266939 A1 | 9/2014 | Baringer et al. |
| 2014/0273858 A1 | 9/2014 | Panther et al. |
| 2014/0275850 A1 | 9/2014 | Venkatraman et al. |
| 2014/0275852 A1 | 9/2014 | Hong et al. |
| 2014/0275854 A1 | 9/2014 | Venkatraman et al. |
| 2014/0276119 A1 | 9/2014 | Venkatraman et al. |
| 2014/0278220 A1 | 9/2014 | Yuen |
| 2014/0278229 A1 | 9/2014 | Hong et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0297217 A1 | 10/2014 | Yuen |
| 2014/0297218 A1 | 10/2014 | Yuen |
| 2014/0305204 A1 | 10/2014 | Hong et al. |
| 2014/0316305 A1 | 10/2014 | Venkatraman et al. |
| 2014/0358012 A1 | 12/2014 | Richards et al. |
| 2015/0025393 A1 | 1/2015 | Hong et al. |
| 2015/0025394 A1 | 1/2015 | Hong et al. |
| 2015/0031967 A1* | 1/2015 | LeBoeuf ............ A61B 5/721 600/301 |
| 2015/0105666 A1 | 4/2015 | Strachan |
| 2015/0122018 A1 | 5/2015 | Yuen |
| 2015/0173631 A1 | 6/2015 | Richards et al. |
| 2015/0196213 A1 | 7/2015 | Pandia et al. |
| 2015/0196256 A1 | 7/2015 | Venkatraman et al. |
| 2015/0201853 A1 | 7/2015 | Hong et al. |
| 2015/0201854 A1 | 7/2015 | Hong et al. |
| 2015/0223708 A1 | 8/2015 | Richards et al. |
| 2015/0230735 A1 | 8/2015 | Venkatraman et al. |
| 2015/0313484 A1* | 11/2015 | Burg ............ A61B 5/0404 600/301 |
| 2015/0314166 A1 | 11/2015 | Hong |
| 2015/0351647 A1 | 12/2015 | Dantu et al. |
| 2016/0029898 A1 | 2/2016 | LeBoeuf et al. |
| 2016/0029964 A1 | 2/2016 | LeBoeuf et al. |
| 2016/0036118 A1 | 2/2016 | Baringer et al. |
| 2016/0038045 A1 | 2/2016 | Shapiro |
| 2016/0051157 A1 | 2/2016 | Waydo |
| 2016/0051158 A1 | 2/2016 | Silva |
| 2016/0051169 A1 | 2/2016 | Hong et al. |
| 2016/0066844 A1 | 3/2016 | Venkatraman et al. |
| 2016/0084869 A1 | 3/2016 | Yuen et al. |
| 2016/0113531 A1 | 4/2016 | Visvanathan et al. |
| 2016/0183818 A1 | 6/2016 | Richards et al. |
| 2016/0302706 A1 | 10/2016 | Richards et al. |
| 2016/0317089 A1 | 11/2016 | Fyfe et al. |
| 2016/0325143 A1 | 11/2016 | Yuen et al. |
| 2016/0361021 A1 | 12/2016 | Salehizadeh et al. |
| 2016/0374621 A1* | 12/2016 | LeBoeuf ............ A61B 5/0059 600/476 |
| 2017/0011210 A1 | 1/2017 | Cheong et al. |
| 2017/0020398 A1 | 1/2017 | Emadzadeh |
| 2017/0027523 A1 | 2/2017 | Venkatraman et al. |
| 2017/0065184 A1 | 3/2017 | Barak |
| 2017/0084983 A1 | 3/2017 | Baringer et al. |
| 2017/0119315 A1 | 5/2017 | LeBoeuf et al. |
| 2017/0143272 A1 | 5/2017 | Brouse |
| 2017/0160398 A1 | 6/2017 | Venkatraman et al. |
| 2017/0188893 A1 | 7/2017 | Venkatraman et al. |
| 2017/0257162 A1 | 9/2017 | Panther et al. |
| 2018/0055450 A1* | 3/2018 | LeBoeuf ............ A61B 5/14551 |
| 2018/0078151 A1* | 3/2018 | Allec ............ A61B 5/681 |
| 2019/0053764 A1* | 2/2019 | LeBoeuf ............ A61B 5/681 |

* cited by examiner

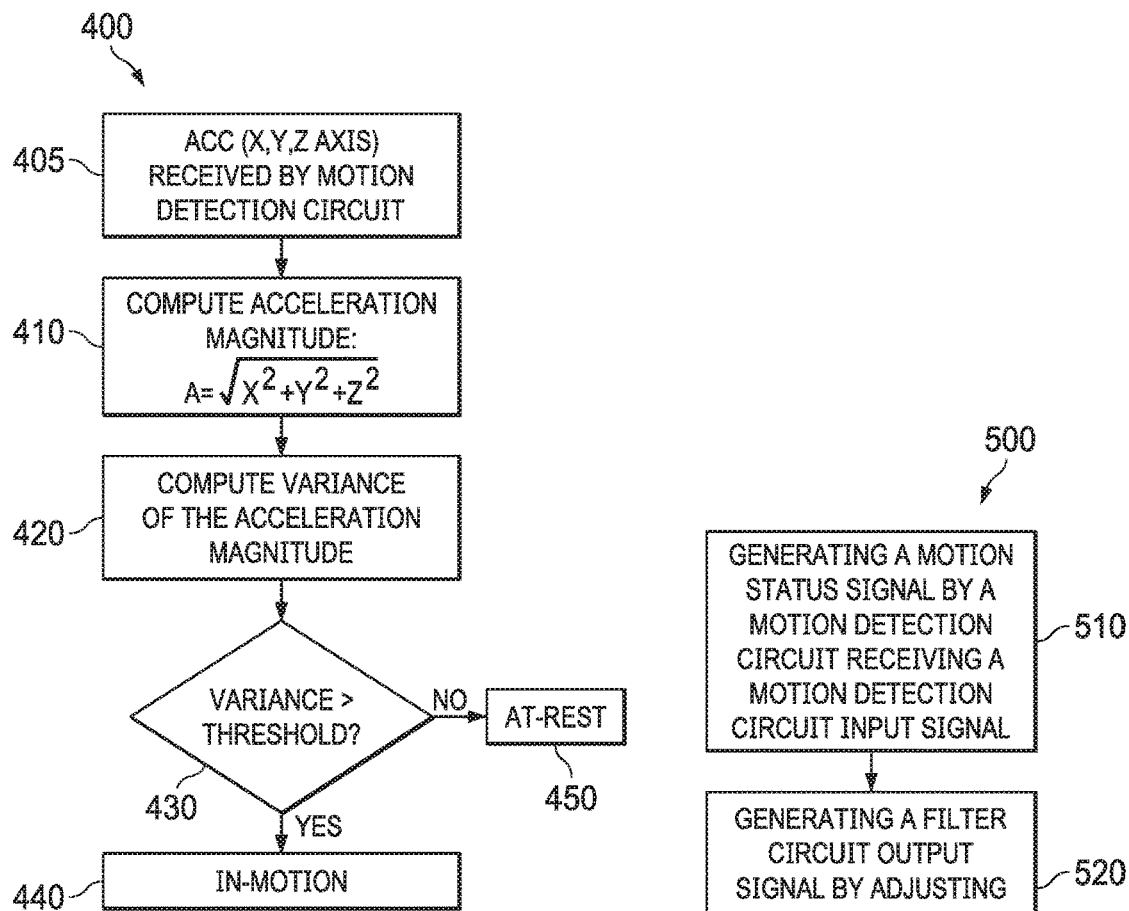
FIG. 4(A)
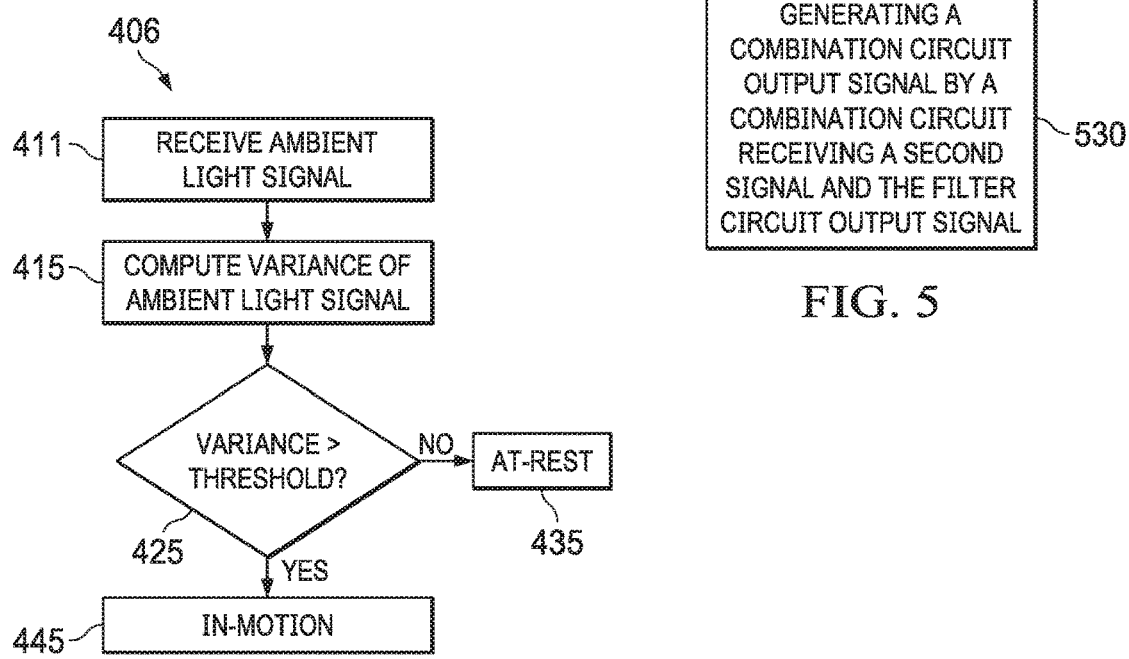
FIG. 4(B)
FIG. 5

MOTION DETECTION AND CANCELLATION USING AMBIENT LIGHT

BACKGROUND

Effective heart rate measurement is an important problem in sports training and in the fitness industry. Traditionally, heart rate monitoring has been performed in a static medical setting by trained professionals. However, recent trends in sports and fitness have created a demand for effective, unsupervised heart rate monitoring in an uncontrolled environment (e.g., during running).

SUMMARY

According to an embodiment, an apparatus to detect a heart rate of a user includes a motion detection circuit configured to generate a motion status signal indicative of a motion status of the user. The apparatus also comprises a filter circuit coupled to the motion detection circuit and configured to generate a filter circuit output signal based on dynamically variable coefficients applied by the filter circuit. The coefficients are dependent on the motion status signal and a first signal received by the filter circuit, the first signal is indicative of motion of the user and ambient light striking the apparatus. In some embodiments, the apparatus also comprises a combination circuit coupled to the filter circuit and configured to receive a second signal indicative of the ambient light, the motion of the user, and non-ambient light reflected from the user, wherein the combination circuit is further configured to determine a difference between the second signal and the filter circuit output signal to generate a combination circuit output signal, the combination circuit output signal indicates the heart rate.

In another embodiment, an apparatus comprises a filter circuit including dynamically adjustable coefficients and configured to receive a first signal during a turn-off period of a light emitting diode (LED) and to generate a filter circuit output signal. The first signal is a representation of ambient light striking the apparatus and a motion signature of a user wearing the apparatus, wherein the LED is configured to emit an LED light toward the user, and wherein the dynamically adjustable coefficients are based at least in part on the first signal. The apparatus also comprises a combination circuit configured to receive a second signal during a turn-on period of the LED, wherein the second signal is indicative of the ambient light, the motion signature of the user and the LED light reflected from the user, wherein the combination circuit is configured to generate a combination circuit output signal representative of the reflected LED light based on the second signal and the filter circuit output signal.

In yet another embodiment, a method includes generating a motion status signal by a motion detection circuit receiving a motion detection circuit input signal, wherein the motion status signal is representative of a motion status of a device containing the motion detection circuit. The method also includes generating a filter circuit output signal by adjusting coefficients in a filter circuit based on the motion status signal, the combination circuit output signal, and a first signal, wherein the first signal is indicative of ambient light striking the device and a motion of the device. The method further includes generating a combination circuit output signal by a combination circuit receiving a second signal and the filter circuit output signal, wherein generating the combination circuit output signal includes determining a difference between the second signal and the filter circuit output signal, wherein the second signal is indicative of the ambient light, the motion of the device, and non-ambient light reflected from the user.

BRIEF DESCRIPTION OF THE DRAWINGS

For a detailed description of various examples, reference will now be made to the accompanying drawings in which:

FIG. 4(a) depicts an illustrative method for using an acceleration signal to detect the motion status of the user, in accordance with various examples;

FIG. 4(b) depicts an illustrative method for using an ambient signal to detect the motion status of the user, in accordance with various examples; and FIG. 5 depicts an illustrative method of generating an output signal that includes heart rate information of the user wearing the wearable device, in accordance with various examples.

DETAILED DESCRIPTION

Figure 1A:
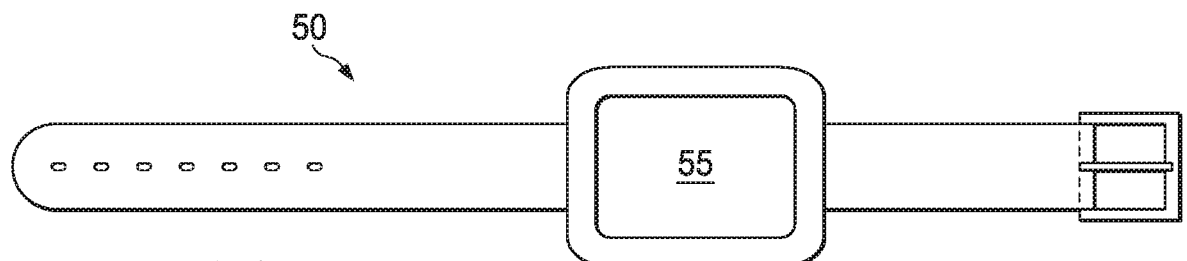
FIG. 1(a) depicts a top-down view of an illustrative wearable device in accordance with various examples.

Pulse oximetry is a non-invasive, light-based technique for measuring the oxygen saturation level of arterial blood and pulse (heart rate). Typically, the sensor portion of a pulse oximeter passes light through blood-perfused tissue, e.g., a finger or an ear lobe, and photoelectrically senses the absorption of light in the tissue. In some cases, the light reflects from the blood-perfused tissue and indicates the absorption of the light in the tissue. Arteries expand and contract due to blood flow and, thus, the amount of light absorbed changes in the course of a heartbeat. The reflected light signal can be analyzed to determine, among other things, the heart rate of the person to which the pulse oximeter is attached. In some cases, the reflected signal is referred to as a photoplethysmograph signal ("PPG signal").

Traditionally, pulse oximetry techniques assume that the person to whom the sensor is attached is stationary and motionless. Thus, such techniques do not account for motion-related noise that may be introduced if the sensor is in motion (e.g., when a user is running). Because these techniques do not properly account for motion-related noise, they produce inaccurate results.

Accordingly, at least some of the examples disclosed herein are directed to systems and methods for identifying and removing noise from heart rate data signals that occur due to motion, thus providing the technical advantage of a more accurate and robust heart rate data signal. The disclosed systems and methods also facilitate the removal of ambient light noise. In particular, the disclosed examples facilitate the removal of ambient light noise and motion noise from a heart rate data signal by using a readily-available ambient light signal that already carries a motion signature.

Illustrative examples include a wearable heart rate monitoring device that emits light from a light emitting diode (LED) toward the user's body (i.e., the user's skin and capillaries) and that includes a sensor (e.g., a photodiode) to sense at least some of the LED light reflected back from the user's body. The sensor also senses ambient light (e.g., sunshine, indoor lighting) striking the sensor. The LED is regularly switched on and off. When the LED is switched on, the sensor receives light composed of reflected LED light and ambient light. If the user is in motion, the sensed light also includes motion noise in the form of a motion signature. When the LED is switched off, the sensor receives light composed of only ambient light. If the user is in motion, this ambient light also carries a motion signature. The heart rate monitoring device is configured to subtract a signal indicating the light sensed when the LED is off from another signal indicating the light sensed when the LED is on to isolate the LED signal. The isolated LED signal contains the desired heart rate data.

Prior to such subtraction, however, an adaptive filter in the heart rate monitoring device filters the signal produced when the LED is off (i.e., the signal composed of only ambient light and a motion signature). The adaptive filter's coefficients may be dynamically adjusted based on whether the heart rate monitoring device is in motion. The adaptive filter processes the signal produced when the LED is off and, in turn, produces a filtered signal that is composed of ambient light noise and motion signature noise. This filtered signal is subtracted from the signal captured when the LED is on, thus producing an output signal from which ambient light noise and motion signature noise have been mostly or completely removed. Although many of the systems and methods are described herein in the context of a wristwatch application, the systems and methods may be adapted as necessary for implementation in any suitable application (e.g., headbands, finger clips, mobile phones, and eyewear).

FIG. 1(a) is a top-down view of an illustrative wearable device 50. The embodiment depicted in FIG. 1(a) is that of a wristwatch, but, as explained, the systems and methods described herein may be implemented in any suitable type of wearable device. The wearable device 50 includes a display 55 to display various types of information, such as e-mail, text messages, and heart rate as determined by the systems and methods described herein.

Figure 1B:
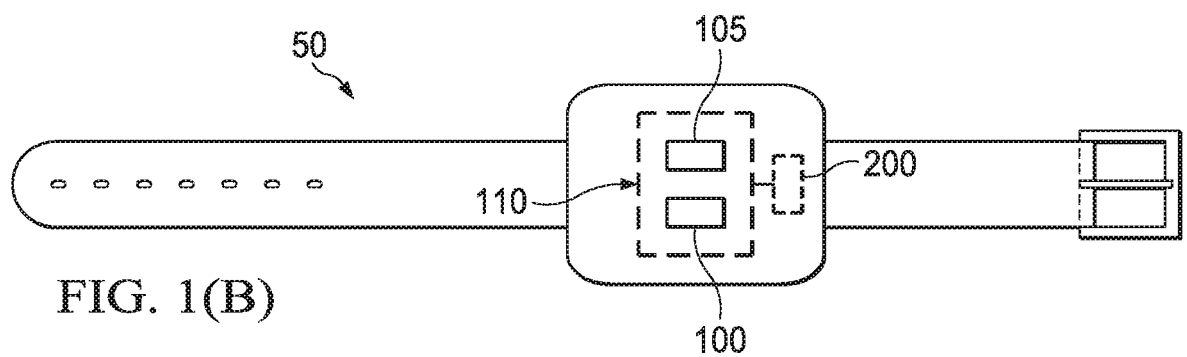
FIG. 1(b) depicts a bottom-up view of the illustrative wearable device of FIG. 1(a), in accordance with various examples.

FIG. 1(b) is a bottom-up view of the wearable device 50. The wearable device 50 includes a sensor unit 110 that couples to a noise cancellation circuit 200 and that is configured to emit and receive light signals. The sensor unit 110 includes a light emitting diode (LED) 105 configured to pass light through a blood vessel in the wrist and a single photodiode 100 configured to detect the wavelength of the light from the LED after it is reflected. In some examples, the sensor unit 110 includes two LEDs—a primary LED and a secondary LED—and a single photodiode arranged to detect the wavelengths of light from both LEDs after it passes through a blood vessel. A LED or LEDs producing light of any suitable wavelength, e.g., red, infrared, blue, etc., may be used. In some examples, the LED employed is an infrared LED. The light sensed by the photodiode 100 is converted into electrical signals that are subsequently provided to the noise cancellation circuit 200 for processing as described below.

Figure 2:
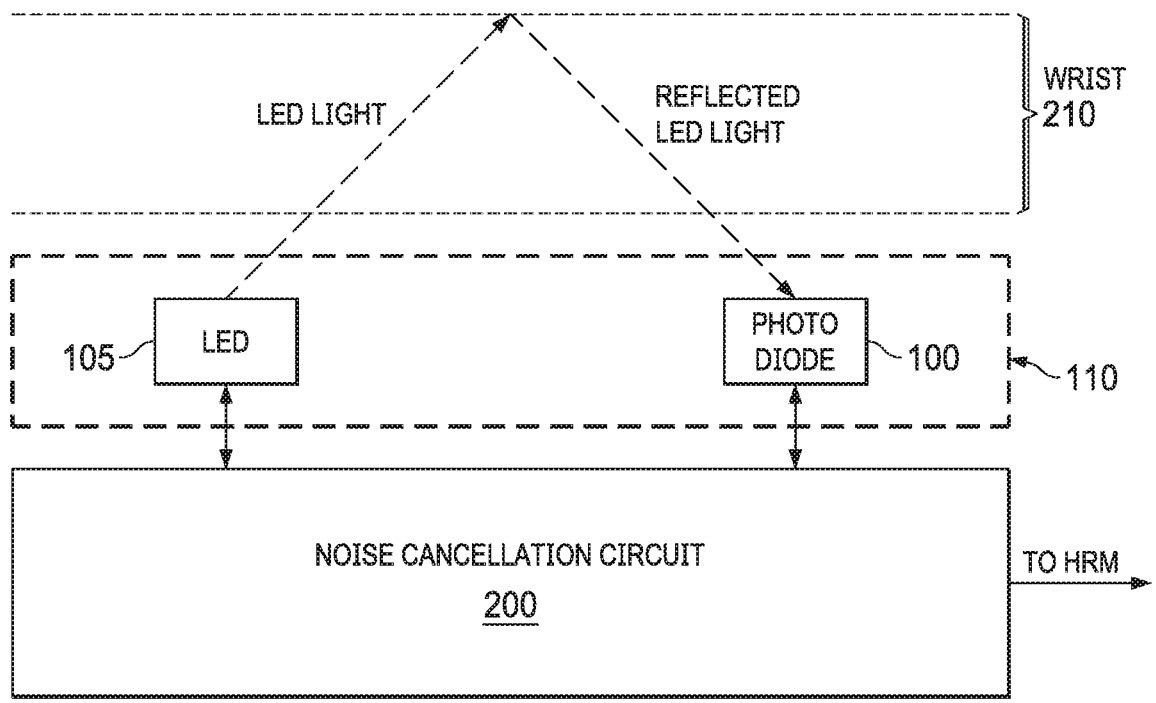
FIG. 2 depicts an illustrative sensor unit and further depicts the interaction of the sensor unit with a portion of the wrist of a user, in accordance with various examples.

FIG. 2 depicts the interaction of the sensor unit 110 with a portion of the wrist 210 of the user. The LED 105 emits an LED light and the portion of the wrist 210 reflects at least some of the LED light. The photodiode 100 receives the reflected LED light containing data corresponding to the heart rate of the user wearing the wearable device 50. In some examples, the reflected LED light can include data related to breathing and other blood-circulatory data of the user. As noted above, the reflected LED light can be corrupted by ambient light and/or motion. When the user wearing the device is stationary (i.e., in an at-rest mode), only ambient light corrupts the reflected LED light. However, a combination of ambient light and motion corrupts the reflected LED light when the user wearing the device is mobile (i.e., in an in-motion mode). Ambient light can refer to any and all sources of light, however minute, that are not supplied by the sensor unit 110.

In some examples, the LED 105 is configured to turn on and turn off at a defined frequency. For example, the LED 105 emits the LED light for a specific amount of time (e.g., 100 microseconds) and then turns off and emits no light for a specific amount of time, for example, 100 microseconds. The LED 105 continuously repeats this on-off pattern, and it may be controlled to switch at a particular frequency (e.g., 100 Hz) based on control signals received from, e.g., a processor in the wearable device 50. For the time period during which the LED 105 is turned on, the photodiode 100 receives a portion of the reflected LED light. In some examples, when the user is in motion, the reflected LED light is corrupted by the ambient light and the motion of the user and the photodiode receives the reflected LED light corrupted with ambient light and motion noise. Similarly, when the user is stationary, the reflected LED light is corrupted just by the ambient light noise.

When the LED 105 is turned off and is not emitting light, the photodiode 100 captures the ambient light striking the photodiode 100. When the user is in motion, the ambient light received by the photodiode 100 includes a motion signature of the user. However, when the user is at rest (i.e., stationary), the photodiode receives only the ambient light. FIG. 2 further includes the noise cancellation circuit 200 to remove noise due to the ambient light and/or motion of the user using the techniques described herein. After removing the noise, the noise cancellation circuit 200 is configured to generate an output signal that is representative of the reflected LED light containing the heart rate of the user. In some examples, the noise cancellation circuit 200 includes various other types of circuitry to facilitate implementation of some or all of the techniques described herein, such as an analog front end circuit, an analog to digital converter circuit, a processor circuit, a memory unit, an accelerometer, and connection interfaces (e.g., Bluetooth unit, USB port, etc.).

Figure 3A:
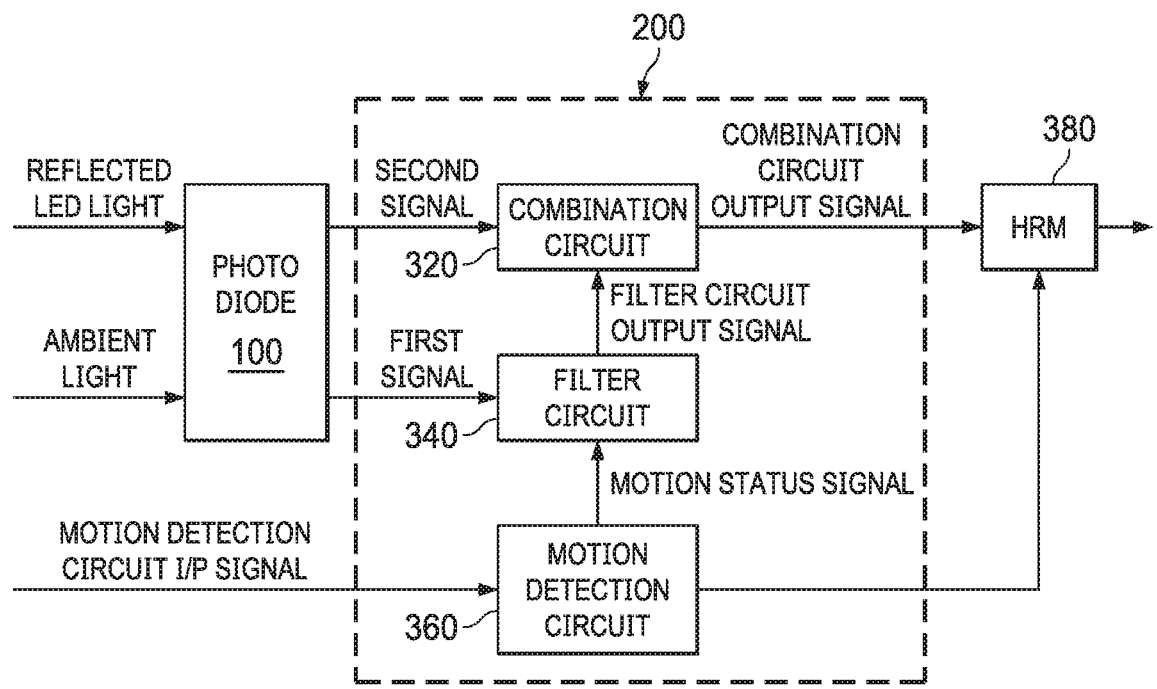
FIG. 3(a) depicts an illustrative block diagram of a noise cancellation circuit, in accordance with various examples.

FIG. 3(a) shows an illustrative block diagram of the noise cancellation circuit 200. The structure of the noise cancellation circuit 200 is described first, followed by a description of the function of the noise cancellation circuit 200. The noise cancellation circuit 200 includes a filter circuit 340, which receives a FIRST SIGNAL and generates a FILTER CIRCUIT OUTPUT SIGNAL (or FILTER OUTPUT SIGNAL or FILTER OUTPUT). The noise cancellation circuit 200 further comprises a combination circuit 320, which receives the FILTER CIRCUIT OUTPUT SIGNAL and a SECOND SIGNAL as inputs. The combination circuit 320 is further configured to generate a COMBINATION CIRCUIT OUTPUT SIGNAL by performing a mathematical function on the FILTER CIRCUIT OUTPUT SIGNAL and the SECOND SIGNAL. The noise cancellation circuit 200 also includes a motion detection circuit 360, which receives a MOTION DETECTION CIRCUIT INPUT SIGNAL and generates a MOTION STATUS SIGNAL that is provided to the filter circuit 340. The FIRST and SECOND SIGNALS are provided to the noise cancellation circuit 200 by the photodiode 100, which receives reflected LED light and ambient light as inputs. The output of the noise cancellation circuit 200 is provided to a heart rate monitor (HRM) 380, which further processes the signal and subsequently outputs the processed signal for display on the display 55 (FIG. 1(a)). In some embodiments, the COMBINATION CIRCUIT OUTPUT SIGNAL includes some signature of the motion signal. Therefore, in such embodiments, the HRM 380 circuit may extrapolate some data from the MOTION DETECTION CIRCUIT 360 and eliminate the motion signal present in the COMBINATION CIRCUIT OUTPUT SIGNAL. The photodiode 100, although it may be used in some examples, does not necessarily reflect an actual implementation. The photodiode 100 is used in FIG. 3(a) to give a conceptual representation of the idea that the reflected LED light and the ambient light require processing before they can be referred to as "signals."

As noted above, the photodiode 100 receives a combination of reflected LED light and ambient light during a turn-on period and receives only ambient light during the turn-off period. Similarly, the photodiode 100 provides the FIRST SIGNAL and the SECOND SIGNAL to the noise cancellation circuit 200 with a period. For example, during a turn-on period of the LED 105, the photodiode 100 provides the noise cancellation circuit 200 with the SECOND SIGNAL and similarly, during a turn-off period of the LED 105, the photodiode 100 provides the noise cancellation circuit 200 with the FIRST SIGNAL. Thus, the FIRST SIGNAL includes only ambient light data (with a motion signature if the user is in motion), and the SECOND SIGNAL includes LED light data and ambient light data (along with the motion signature if the user is in motion). In some embodiments, one or more of the combination circuit 320 and the filter circuit 340 comprises a buffer to facilitate the simultaneous processing of the FIRST and SECOND SIGNALS by the filter circuit 340 and the combination circuit 320, respectively.

The motion detection circuit 360 receives the MOTION DETECTION CIRCUIT INPUT SIGNAL and is configured to recognize the state (in-motion or at-rest) of the user wearing the wearable device 50 based on that signal. The motion detection circuit 360 may comprise any components suitable for implementing the functions attributed herein to that component—for example, storage comprising executable code, a processor to execute the executable code, etc. In some examples, the MOTION DETECTION CIRCUIT INPUT SIGNAL comprises an accelerometer signal. The wearable device 50 may include an accelerometer which generates the accelerometer signal including components in a coordinate system. The coordinate system used may be any suitable coordinate system, such as a Cartesian coordinate system, a cylindrical coordinate system, a spherical coordinate system, a polar coordinate system, a homogeneous coordinate system, etc.

In some embodiments, the MOTION DETECTION CIRCUIT INPUT SIGNAL may comprise an ambient light signal, which may be encoded with a motion signature. In such embodiments, the MOTION DETECTION CIRCUIT INPUT SIGNAL may be the FIRST SIGNAL provided by the photodiode 100. The remainder of this disclosure assumes that the MOTION DETECTION CIRCUIT INPUT SIGNAL comprises an accelerometer signal based on a Cartesian coordinate system, although the scope of this disclosure is not limited as such. The principle used by the motion detection circuit 360 to detect the motion state of the user is now explained with reference to FIGS. 4A and 4B.

The method 400 described in FIG. 4A utilizes the accelerometer signal which, as noted above, indicates the acceleration of the user wearing the wearable device 50 in the X, Y and Z directions. The accelerometer signal—ACC(X, Y, Z)—is received by the motion detection circuit 360 in step 405. The step 410 includes computing an acceleration magnitude of the received ACC(X, Y, Z) signal. The acceleration magnitude is typically computed by finding a square root of a summation of the $X^2$, $Y^2$, and $Z^2$ components of the received ACC(X, Y, Z) signal. In some embodiments, the acceleration magnitude can be computed using the variance of $X^2+Y^2+Z^2$. Using this algebraic expression eliminates the need to perform a square root operation, which can reduce overall hardware overhead. The algebraic expression disclosed in the step 410 is not limiting, any suitable expression that can utilize the accelerometer signal ACC(X, Y, Z) to computer the acceleration magnitude can be utilized. The method 400 continues in step 420 with computing an acceleration variance value of the acceleration magnitude computed in the step 410. The method 400 continues in block 430 with comparing the acceleration variance value with the threshold value. In response to the determination that the acceleration variance value is higher than the threshold, the motion detection circuit 360 is configured to generate a motion status signal indicating that the user is in motion (step 440). However, if the variance value is less than the threshold, the motion detection circuit 360 is configured to generate a motion status signal indicating that the user is at rest (step 450).

As mentioned, in some examples, the motion detection circuit 360 utilizes an ambient light signal to detect the motion state of the user. In such examples, the motion detection circuit 360 performs a method 406 as described in FIG. 4(b). The method 406 comprises receiving an ambient light signal at step 411. Step 415 computes an ambient light signal variance value of the ambient light signal received. The method 406 continues in block 425 with comparing the ambient light signal variance value with a threshold value. In response to the determination that the ambient light signal variance value is higher than the threshold, the motion detection circuit 360 is configured to generate a motion status signal indicating that the user is in motion (step 445). However, if the ambient light signal variance value is less than the threshold, the motion detection circuit 360 is configured to generate a motion status signal indicating that the user is at rest (step 435).

In some examples, the motion detection circuit 360 utilizes the ambient light signal to detect the motion state of the user by computing a Fast Fourier Transform ("FFT") of the MOTION DETECTION CIRCUIT INPUT SIGNAL. The motion detection circuit 360 may perform an FFT operation on the ambient signal, which may provide amplitude-frequency data related to the ambient signal. In some examples, this amplitude-frequency data can be further utilized to extrapolate peaks corresponding to the amplitude-frequency data. The extrapolated peaks may be further used to detect the motion status of the user. For instance, if at least one of the peaks is above a pre-defined threshold, the motion detection circuit 360 generates the MOTION STATUS SIGNAL indicating that the user is in-motion. On the other hand, if all the peaks are below the pre-defined threshold, the MOTION STATUS SIGNAL indicates that the user is at-rest. In some examples, additional information can be extrapolated from the FFT operation. For example, a peak typically occurs at a frequency, and it indicates the frequency of the motion signature/component, which results in the peak. In some examples, the frequency corresponds to a harmonic frequency, i.e., the motion signature may have finite amplitude (and a peak) at a harmonic frequency. The frequency locations of these harmonics may be stored in the HRM 380, and the HRM 380 may further utilize the stored information regarding the harmonic frequency to further eliminate any motion signature that may have been passed undetected through the filter circuit 340.

Referring back to FIG. 3(a), in some examples, the filter circuit 340 is an adaptive filter, meaning that it is a self-optimizing filter whose filter coefficients may be dynamically modified as desired. These dynamically modifying coefficients are sometimes referred to as dynamically variable coefficients. The filter circuit 340 bases its filter coefficients upon measured statistical characteristics of the current value of FIRST SIGNAL and the previous values of the FIRST SIGNAL portions of which may be stored in a buffer in the filter circuit 340), as well as upon the MOTION STATUS SIGNAL received from the motion detection circuit 360. The filter circuit 340 is configured to dynamically modify its coefficients using a recursive algorithm that adjusts and updates the filter coefficients with the arrival of each new input (FIRST SIGNAL) based on the current value of the FIRST SIGNAL, the previous values of FIRST SIGNAL contents stored in the internal buffer, and the MOTION STATUS SIGNAL.

In particular, the filter circuit 340 receives the MOTION STATUS SIGNAL indicating to the filter circuit 340 the motion state of the user. Responsive to receiving a MOTION STATUS SIGNAL indicating that the user is in motion, the filter circuit 340, because of its adaptive nature, is configured to adapt its filter coefficients based on the FIRST SIGNAL and the buffer-stored value(s) of the FIRST SIGNAL. Altering the coefficients assists the filter circuit 340 to capture both the motion signature and the ambient signal from the FIRST SIGNAL and to generate the FILTER CIRCUIT OUTPUT SIGNAL that is accurately representative of the motion noise and the ambient light noise corrupting the reflected LED light received by the photodiode 100 during an in-motion state of the user. However, responsive to receiving a MOTION STATUS SIGNAL indicating that the user is at rest, the filter circuit 340 is configured to modify its filter coefficients to pre-programmed values. Altering the filter coefficients to pre-programmed values captures the ambient light signal from the FIRST SIGNAL and facilitates the generation of the FILTER CIRCUIT OUTPUT SIGNAL representative of the ambient light noise corrupting the reflected LED light received by the photodiode 100 in the at-rest state of the user. Combination circuit 320 receives the FILTER CIRCUIT OUTPUT SIGNAL and the SECOND SIGNAL and performs a mathematical function (e.g., subtraction) on both of the received signals to generate the COMBINATION CIRCUIT OUTPUT SIGNAL, which includes information regarding the heart rate of the user wearing the wearable device 50.

Figure 3B:
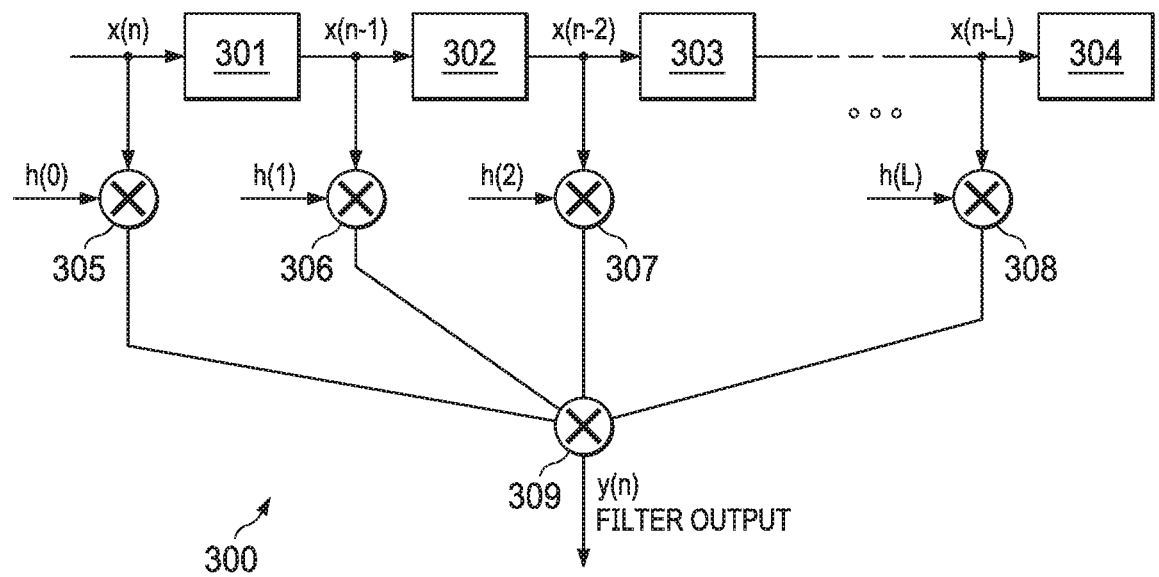
FIG. 3(b) depicts an illustrative tap filter, in accordance with various examples.

Refer now to FIG. 3(b), which depicts an illustrative L+1 tap filter 300 that may be used in the filter circuit 340. In some examples, the tap filter 300 may be an adaptive filter. In the tap filter 300, "L" may determine the number of coefficients the tap filter 300 may include. The tap filter 300 may also include processing blocks 301, 302, 303, 304, which receives the input signals x(n), x(n−1), x(n−2), x(n−L) (respectively). In some examples, the processing blocks 301, 302, 303, 304 may perform an inverse-Z function to each of their inputs. The tap filter 300 may also include blocks 305, 306, 307, 308 that perform a mathematical function (such as multiplication). The tap filter 300 also includes a block 309 that perform another mathematical function (such as addition). In some examples, the blocks 305, 306, 307, 308, 309 collectively perform a convolution function. The coefficients of the tap filter 300 can be represented as $h_0, h_1, h_2, \ldots h_L$, which further may be the input to the blocks 305, 306, 307, 308 (respectively). In operation, if the FIRST SIGNAL is represented as samples $x_0, x_1, x_2, x_3, \ldots$ corresponding to time indices 0, 1, 2, 3 . . . and the FILTER CIRCUIT OUTPUT SIGNAL (or filter output or filter output signal) is represented as $y_0, y_1, y_2, y_3, \ldots$, then the filter circuit 340 output is the convolution of the filter input with the filter coefficients and is mathematically given by:

$$y(n) = \sum_{k=0}^{L} h(k)x(n-k)$$

In some examples, the coefficients of the tap filter 300 are time-varying and can be adapted based on the difference between the SECOND SIGNAL and the FILTER CIRCUIT OUTPUT SIGNAL, as the ERROR SIGNAL (not expressly shown).

In some examples, the coefficients h(n), n=0, 1, ... L can be varied by an adaptive filter mechanism. In some embodiments, the filter circuit 340 is adapted by a Recursive Least Squares (RLS) mechanism, in which the difference between the SECOND SIGNAL and the FILTER CIRCUIT OUTPUT SIGNAL forms an ERROR SIGNAL that is used to train the circuit filter coefficients.

Still referring to FIG. 3(a), the HRM 380 can be used to estimate the heart rate. The HRM 380 may use different approaches to monitor the heart rate. In some examples, the operation of the HRM 380 can be based on a frequency domain approach. When the user is at-rest, the HRM 380 may perform a Fast Fourier Transform FFT on the COMBINATION CIRCUIT OUTPUT SIGNAL. The COMBINATION CIRCUIT OUTPUT SIGNAL samples are collected in a buffer (not expressly shown) in the HRM 380 and only after an initial latency period (e.g., 5 seconds); the HRM 380 begins performing the FFT on the signal. From that point forward, a sliding window FFT may be taken every second. If, for instance, the pulse repetition frequency (PRF) is 25 Hz, then the first FFT may be started only after 125 samples are collected. Subsequently, for every second, 25 new samples may be added to the 125 sample buffer in a sliding window manner, replacing the oldest 25 sample data. In an example, the HRM 380 performs a 512-point FFT on the 125 sample data with zero padding. To estimate the heart rate, the periodogram-based approach may be used. The COMBINATION CIRCUIT OUTPUT SIGNAL, once transformed by the HRM 380 FFT process, may be squared by the HRM 380 to compute the power spectral density (PSD). The peak in the PSD provides an estimate of the heart rate signal. Accordingly, the HRM 380 may search and select the peak in the PSD.

As mentioned, when the user is at-rest, the peaks in the Fast-Fourier-transformed COMBINATION CIRCUIT OUTPUT SIGNAL provide the estimates of the heart rate. Stated another way, the frequency location of the peak in the Fast-Fourier-transformed COMBINATION CIRCUIT OUTPUT SIGNAL corresponds to the frequency of the heart rate signal. In some examples, to compute the heart rate in beats per minute, the frequency of heart rate signal may be multiplied by 60.

A peak search algorithm can also be used in the HRM 380. The peak search algorithm may be split into two phases, i.e., acquisition and tracking. In the acquisition phase, the HRM 380 assumes that the user is at-rest and searches for peaks in the COMBINATION CIRCUIT OUTPUT SIGNAL PSD. In the tracking phase, the HRM 380 searches for peaks in the COMBINATION CIRCUIT OUTPUT SIGNAL near the peaks of the acquisition frequency or at some previously stored frequencies. In the tracking phase if the user is in-motion, the FFT of the both the COMBINATION CIRCUIT OUTPUT SIGNAL and the FILTER CIRCUIT OUTPUT SIGNAL is computed in HRM 380 and can be used to determine the heart rate of the user. In some embodiments, if the MOTION DETECTION CIRCUIT INPUT SIGNAL is based on accelerometer signal then FFT of the COMBINATION CIRCUIT OUTPUT SIGNAL and MOTION DETECTION CIRCUIT INPUT SIGNAL is computed in HRM 380 and can be used to determine the heart rate of the user.

FIG. 5 depicts a method 500 of generating an output signal (e.g., the COMBINATION CIRCUIT OUTPUT SIGNAL depicted in FIG. 3(a)) indicating the heart rate of the user wearing the wearable device 50. The method 500 is described in tandem with FIG. 3(a). Method 500 begins in step 510 with generating a MOTION STATUS SIGNAL representative of the user's motion status (e.g., in-motion, at-rest) using the motion detection circuit 360. In some examples, the motion detection circuit 360 receives the MOTION DETECTION INPUT SIGNAL through an accelerometer. In other examples, the MOTION DETECTION INPUT SIGNAL is an ambient light signal indicative of the ambient light present around the wearable device 50. The method 500 continues in step 520 with generating a FILTER CIRCUIT OUTPUT SIGNAL by adjusting the coefficients in the filter circuit 340. In some examples, the FILTER CIRCUIT OUTPUT SIGNAL depends on one or more of the FIRST SIGNAL, a previous (e.g., buffered) value of the FILTER CIRCUIT OUTPUT SIGNAL, and/or the MOTION STATUS SIGNAL received by the filter circuit 340.

As noted above, the MOTION STATUS SIGNAL indicates to the filter circuit 340 the motion state of the user. Responsive to receiving the MOTION STATUS SIGNAL indicating that the user is in motion, the filter circuit 340 is configured to adapt its filter coefficients (and any other suitable internal adjustment settings) based on the current value of the FIRST SIGNAL and the buffered values of prior FIRST SIGNAL. In some embodiments, the filter circuit 340 is adapted by a Recursive Least Squares (RLS) mechanism. The FILTER CIRCUIT OUTPUT SIGNAL is based on the current and previous values of the FIRST SIGNAL. The difference between the second signal and the FILTER CIRCUIT OUTPUT SIGNAL forms the ERROR SIGNAL which is used to adapt the circuit filter coefficients. Altering the filter coefficients assists the filter circuit 340 to capture both the motion signature and the ambient light signal from the FIRST SIGNAL and to generate the FILTER CIRCUIT OUTPUT SIGNAL, which accurately represents the motion noise and the ambient light noise corrupting the reflected LED light received by the photodiode 100 when the user is in motion.

However, responsive to receiving a MOTION STATUS SIGNAL indicating that the user is at rest, the filter circuit 340 is further configured to adapt the filter circuit 340 coefficients to pre-programmed values. Altering the filter coefficients to pre-programmed values captures the ambient light signal from the FIRST SIGNAL and generates the FILTER CIRCUIT OUTPUT SIGNAL, which accurately represents the ambient light noise corrupting the reflected LED light received by the photodiode 100 when the user is at-rest. In the case the user is at rest, the filter circuit 340 coefficients are programmed such that only one of the coefficients is programmed to a fixed value of 1 and all the other coefficients are programmed to zero. In some embodiments, to ensure that the group-delay of the filter circuit 340 remains the same for the in-motion and at-rest case, center coefficient of the filter circuit 340 can be programed to be 1 and other coefficients to be zero. For example, if the filter circuit is a 17-tap filter and its coefficients are represented as $h_0, h_1, h_2, \ldots h_L$, (L=16), then in at-rest case the coefficient $h_8$ is programmed to be 1 and all other coefficients are programmed to zero.

The method 500 further continues in step 530 with generating the COMBINATION CIRCUIT OUTPUT SIGNAL by a combination circuit 320 receiving the SECOND SIGNAL and the FILTER CIRCUIT OUTPUT SIGNAL. Specifically, the combination circuit 320 receives the FILTER CIRCUIT OUTPUT SIGNAL and the SECOND SIGNAL and performs a mathematical function (e.g., subtraction) on both received signals to generate the COMBINATION CIRCUIT OUTPUT SIGNAL, which includes information regarding the heart rate of the user wearing the wearable device 50.

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

What is claimed is:
1. An apparatus to detect a heart rate of a user, comprising:
a motion detection circuit having an input coupled to a motion detection signal and an output wherein the output is configured to generate a motion status signal indicative of a motion status of the user;
a filter circuit having a first input, a second input and an output wherein the first input is coupled to the output of the motion detection circuit wherein the output of the filter circuit is configured to generate a signal based on dynamically variable coefficients applied by the filter circuit, wherein the coefficients are dependent on the motion status signal and a first signal received by the second input of the filter circuit, wherein the first signal is indicative of motion of the user and ambient light striking the apparatus; and
a combination circuit having a first input, a second input and an output wherein the first input of the combination circuit is coupled to the output of the filter circuit, and the second input of the combination circuit is configured to receive a second signal indicative of the ambient light, the motion of the user, and non-ambient light reflected from the user, wherein the combination circuit is further configured to determine a difference between the second signal and the filter circuit output signal to generate an output signal from the output of the combination circuit, wherein the output signal from the output of the combination circuit indicates the heart rate;
wherein the motion detection circuit is further configured to compute a Fast Fourier Transform (FFT) of the motion detection circuit input signal to generate a peak, wherein the motion detection circuit is configured, in response to the peak being less than a pre-defined threshold, to generate the motion status signal to indicate that the user is resting; and in response, to the peak being greater than the pre-defined threshold, to generate the motion status signal to indicate that the user is moving.

2. The apparatus of claim 1, wherein the motion detection circuit is further configured to receive a motion detection circuit input signal which is selected from the group consisting of an accelerometer signal and the first signal.

3. The apparatus of claim 1, wherein the motion detection circuit is further configured to compute a variance value, wherein:
in response to the variance value being greater than a threshold value, the motion status signal causes the filter circuit to adjust the dynamically variable coefficients; and
in response to the variance value being less than the threshold value, the motion status signal causes the filter circuit to adjust the dynamically variable coefficients to a fixed value.

4. The apparatus of claim 1, wherein the combination circuit output signal is a representation of the non-ambient light reflected from the user.

5. The apparatus of claim 1, wherein the non-ambient light is a light emitting diode (LED) light reflected from the user.

6. A method, comprising:
generating a motion status signal by a motion detection circuit receiving a motion detection circuit input signal, wherein the motion status signal is representative of a motion status of a device containing the motion detection circuit;
generating a filter circuit output signal by adjusting coefficients in a filter circuit based on the motion status signal, a combination circuit output signal, and a first signal, wherein the first signal is indicative of ambient light striking the device and a motion of the device; and
generating a combination circuit output signal by a combination circuit receiving a second signal and the filter circuit output signal, wherein generating the combination circuit output signal includes determining a difference between the second signal and the filter circuit output signal, wherein the second signal is indicative of the ambient light, the motion of the device, and non-ambient light reflected from the user;
further comprising, by the motion detection circuit;
computing a Fast Fourier Transform (FFT) of the motion detection circuit input signal to generate a peak, wherein the motion detection circuit is configured, in response to the peak being less than a pre-defined threshold, to generate the motion status signal to indicate that the user is resting; and
in response, to the peak being greater than the pre-defined threshold, to generate the motion status signal to indicate that the user is moving.

7. The method of claim 6 wherein:
in response to the motion status signal indicating that the user is resting, adjusting the coefficients to a fixed value; and
in response to the motion status signal indicating that the user is moving, adjusting the coefficients based on the first signal and the combination circuit output signal.

8. The method of claim 6, wherein the motion detection circuit input signal is selected from the group consisting of an accelerometer signal and the first signal.

9. The method of claim 8 further comprising:
computing, by the motion detection circuit, a first signal variance value;
in response to the first signal variance value being lower than a threshold value, causing the filter circuit to adjust the coefficients to a fixed value representative of the device in a stationary state; and
in response to the first signal variance value being greater than the threshold value, causing the filter circuit to adjust the coefficients based on the first signal and the combination circuit output signal.

10. The method of claim 8 further comprising:
computing, by the motion detection circuit, an acceleration magnitude by performing an algebraic operation on X, Y, and Z components of the accelerometer signal; and
computing, by the motion detection circuit, an accelerometer variance value of the acceleration magnitude.

11. The method of claim 10, wherein:
in response to the accelerometer variance value being lower than a second threshold value, causing the filter circuit to adjust the coefficients to a fixed value representative of the device in a stationary state; and
in response to the accelerometer variance value being greater than the threshold value, causing the filter circuit to adjust the coefficients based on the first signal and the combination circuit output signal.

* * * * *